United States Patent [19]
Mohebati et al.

[11] Patent Number: 5,636,238
[45] Date of Patent: Jun. 3, 1997

[54] DEVICE FOR PRODUCING LASER RADIATION AT A VARIABLE OR SELECTABLE WAVELENGTH

[75] Inventors: Arman Mohebati, Romiley; John Colles, Biggar; Andrew Berry, Knutsford, all of Great Britain

[73] Assignee: Lynton Lasers Limited, Manchester, United Kingdom

[21] Appl. No.: 518,915

[22] Filed: Aug. 24, 1995

[30] Foreign Application Priority Data

Jan. 16, 1995 [GB] United Kingdom ............... 9500753

[51] Int. Cl.$^6$ ............................................. H01S 3/20
[52] U.S. Cl. ................. 372/54; 372/23; 372/102; 372/92; 372/22; 372/34; 372/35
[58] Field of Search ........................ 372/534, 23, 102, 372/34, 35, 22, 92

[56] References Cited

U.S. PATENT DOCUMENTS

| | | | |
|---|---|---|---|
| 4,627,068 | 12/1986 | Johnson et al. | 372/54 |
| 4,661,958 | 4/1987 | Bowes et al. | 372/34 |
| 4,723,257 | 2/1988 | Baer et al. | 372/92 |
| 4,852,114 | 7/1989 | Karube | 372/34 |
| 4,933,949 | 6/1990 | Johnson | 372/23 |
| 5,066,291 | 11/1991 | Stewart . | |
| 5,087,388 | 2/1992 | Mahoney et al. | 372/54 |
| 5,144,638 | 9/1992 | Davin | 372/54 |
| 5,249,192 | 9/1993 | Kuizenga et al. . | |
| 5,977,746 | 12/1991 | Ewart | 372/54 |

FOREIGN PATENT DOCUMENTS

| | | |
|---|---|---|
| 0 429 297 A2 | 5/1991 | European Pat. Off. . |
| 1 552 030 | 9/1979 | United Kingdom . |
| 2 190 784 | 11/1987 | United Kingdom . |

*Primary Examiner*—Leon Scott, Jr.
*Attorney, Agent, or Firm*—J. Zackery Legal Group

[57] ABSTRACT

A device permitting a single primary laser producing a collimated beam at a given wavelength, to be used for different purposes by converting the collimated beam to a beam of different wavelength. The device comprises a secondary laser disposed within a body removably attached to the distal end of an articulated arm delivery system attached to the primary laser. Preferably, the secondary laser is interchangeable with respect to the delivery system thus to extend the wavelength (color) coverage of the primary laser according to the required wavelength conversion. The secondary laser may include an optical crystal or a circulated organic dye solution within a removable cell or reservoir. Appropriate lenses are provided to focus the primary beam and to determine the spot diameter of the conversed beam.

28 Claims, 3 Drawing Sheets

DEVICE FOR PRODUCING LASER RADIATION AT A VARIABLE OR SELECTABLE WAVELENGTH

BACKGROUND TO THE INVENTION

1. Field of the Invention

THIS INVENTION concerns a device for producing laser radiation at a wavelength which may be selected from a basic wavelength emitted by a single laser.

The use of lasers in medicine and surgery has become wide spread and with the availability of new lasers providing different wavelengths and pulse lengths, new applications for these devices have been established. The use of lasers in dermatology in particular has become very wide spread and many skin conditions such as pigmented lesions, vascular lesions and tattoos can be treated successfully with various lasers. Due to the nature of the interaction of the laser light with the skin and its various constituents, different wavelengths of laser light are required for different forms of treatment. Currently, a range of lasers are needed by the dermatologist to allow him to treat a wide range of skin disorders. The high costs and required space associated with acquiring and operating several lasers often impose a limitation on the usefulness of lasers for dermatological procedures. A single device capable of producing several wavelengths would clearly offer many advantages.

2. Summary of the Prior Art

A preferred laser device used in medical treatment comprises a laser for generating a beam of laser light, and a delivery system for receiving light from the laser and re-emitting it at a treatment site; wherein the delivery system comprises a plurality of hingedly interconnected arms through which the laser light may pass, reflecting elements being disposed at the interconnections to direct the beam from one arm to the next. However, in such devices, it has been found that the reflective elements must be selected to operate efficiently with a particular wavelength of laser light, making this articulated arm type system suited for delivery of laser light of just one wavelength, and precluding its use with known lasers which are capable of output of laser light of multiple wavelengths.

It is an aim of this invention to provide a laser device incorporating an articulated arm type delivery system which is capable of producing laser light for treatment of more than one wavelength.

SUMMARY OF THE INVENTION

According to the invention, there is provided a device for producing laser light of a variable or selectable wavelength comprising a primary laser; a multi-directional delivery system, the delivery system including a linear articulated arm; and a conversion device; wherein a beam of primary laser light emitted from the primary laser is transmitted through the articulated arm to be received by the conversion device, from which a secondary laser beam of a different wavelength is emitted.

Preferably, the conversion means operates by laser action, fluorescence conversion or non-linear processes.

The device can have applications in several areas including dermatology where the wavelength of the laser may be altered to match the absorption of specific constituents of skin.

The wavelength of the laser radiation is converted by a medium which can be an inorganic solid fluorescent material, an organic dye solution, a polymer doped with fluorescent organic dyes or porous glasses doped with organic dyes or inorganic fluorescent materials, or a non-linear optical crystal.

The laser which acts as the pump laser can be a flashlamp pumped, Q-switched, frequency doubled, Nd:YAG laser, a CW, Q-switched, frequency doubled, Nd:YAG laser, a copper vapour laser, or a flashlamp pumped dye laser, for example.

The device is configured in modular form to allow easy attachment to the distal end of an articulated arm system used for medical applications, allowing additional wavelengths to be obtained from existing lasers. The device can be easily and quickly installed at the end of the articulated arm, requiring no optical alignment. This would allow the change of wavelength during clinical procedures with minimum delay and inconvenience.

The configuration and optical arrangement of the device can vary according to which medium is used for converting the laser wavelength.

DETAILED DESCRIPTION OF THE PREFERRED EMBODIMENTS

Figure 1:
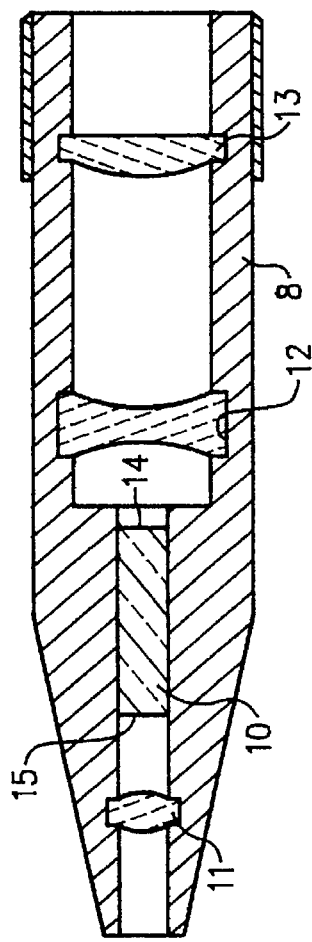
FIG. 1 is a cross-section through a device for attachment the distal end of an articulated arm delivery system of a laser.

Referring now to FIG. 1, there is shown a device for converting the wavelength of the radiation delivered through an articulated arm system from a flashlamp pumped, Q-switched, frequency doubled Nd:YAG laser, into radiation in the near-IR part of the spectrum (790 nm). The device used for converting the laser radiation is, in effect, a secondary laser in the form of a Titanium doped sapphire crystal 10. Other laser crystals such as Alexandrite, Forsterite, etc. can be used to provide other wavelengths.

The device, which is enclosed within a modular body 8 to be removably attached to the distal end of the articulated arm system (not shown), includes optical elements 11, 12 and 13 for adjusting the beam diameter to the appropriate size. Due to the lower absorption coefficient of the Titanium doped sapphire crystal 10 compared to, for example, laser dyes it is necessary to adopt a longitudinal pumping arrangement. This provides a longer absorption path length for the pump laser radiation allowing better absorption of the radiation within the crystal. The crystal is positioned in the path of the beam as shown in FIG. 1. The end faces 14 and 15 of the crystal are cut parallel (~1 mrad) and optically polished. The crystal is positioned so that the end faces are perpendicular to the optical axis of the device and the articulated arm, to within 5 mrad.

On the proximal end face 14 of the crystal there is provided a dielectric coating of low reflectivity (less than 25%) at 532 nm and maximum reflectivity (more than 95%) at 790 nm. On the distal end 15, there is provided a dielectric coating of partial reflectivity (between 30% and 95%) at the same near-IR wavelength. The reflectivity of this latter coating is chosen such that it will optimise the energy extraction from the device. In this way the crystal faces form an optical resonator creating laser action in the optically excited crystal material. High damage threshold coatings are used to avoid optical damage from the pump laser radiation on the near face of the crystal and from the Titanium sapphire laser radiation on the other face of the crystal. The lasing medium properties such as length, dopant concentration, etc., are chosen to allow maximum conversion of the pump light into laser radiation at the lasing wavelength of the material used. These parameters vary for different pump energies. The crystal length may be in the range 5 mm to 50 mm. The dopant concentration may be in the range 0.05% to 0.25%.

A quarter wave plate is used to convert the linear polarisation of the pump laser into circular polarisation before the articulated arm. This is essential as the absorption in the Titanium doped sapphire crystal is polarization-dependent and the articulated arm rotates the plane of polarisation as it is moved. This would lead to variations in the absorption of the pump radiation within the crystal when the articulated arm is moved if linearly polarised pump radiation were used. This variation in the absorbed pump power would in turn lead to variations in the output power of the device.

The generated near-IR beam is focused by the lens 11 to provide a specified beam diameter at a given distance from the end of the device, allowing a known energy density to be delivered to the area under treatment. Again a choice of lenses with different focal lengths would allow a wide range of spot sizes and energy densities to be obtained.

Figure 2:
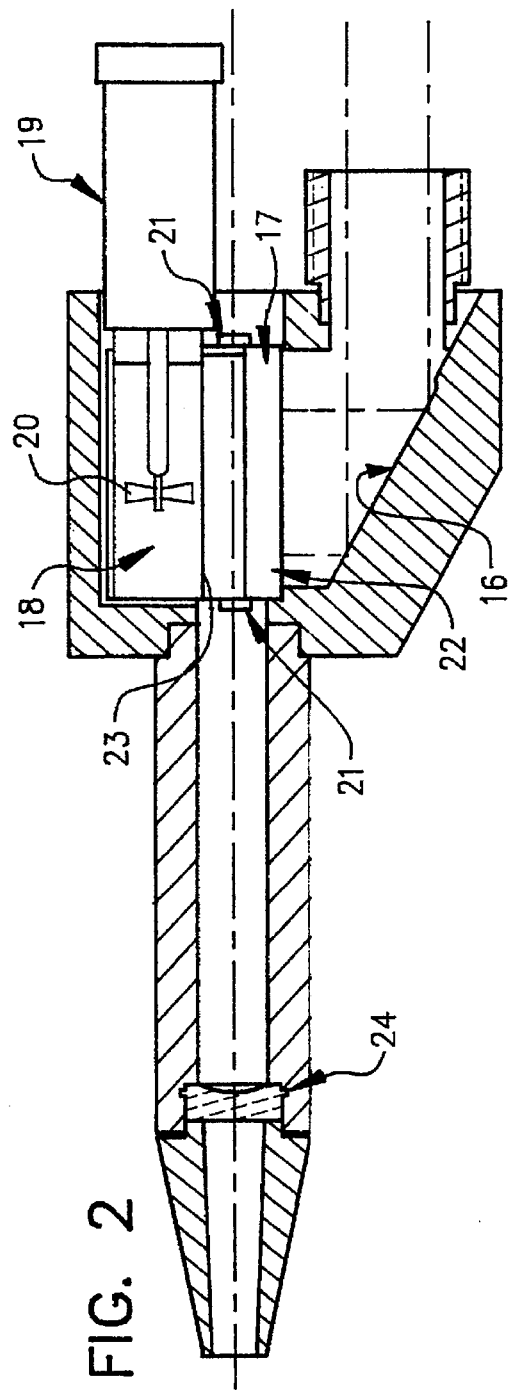
FIG. 2 is a similar view of a second embodiment of the invention.

A side pumping arrangement similar to the geometry to be described in relation to FIG. 2 is possible for strongly absorbing crystals. TiS crystals with high dopant levels allowing full absorption of the pump beam in a side pumping geometry are becoming commercially available.

Referring now to FIG. 2 there is shown a modular device for converting the radiation delivered through an articulated arm system from a frequency doubled Nd:YAG laser into radiation in the visible and near-IR part of the spectrum. The device incorporates an organic dye solution as the wavelength conversion medium. The generated wavelength is determined by the Choice of the dye used, and can be in the range of 550 nm to 750 nm. Pulse energy for the pump laser can be in the range of 50 mJ to 500 mJ. Pulse length for the pump laser will be in the range 1 ns to 50 ns. The device efficiency for the conversion of the pump wavelength to the new wavelength can be in the range 10% to 70%.

The radiation from the frequency doubled Nd:YAG laser is expanded and simultaneously deflected using a diffraction grating 16 optically to excite an organic dye solution contained within a glass tube 17 having a central bore of 3 mm diameter. The dye solution is constantly circulated through this bore and replenished with fresh dye solution contained in a small removable reservoir 18. This circulation is achieved by means of a battery powered DC motor 19 driving a spinning mechanism in the form of a propeller 20 which circulates the dye through the reservoir and the glass tube. The ends of the tube 17 are sealed with mirrors 21 thus to form an optical resonator. The ends of the tube are machined and polished parallel (−1 mR) to avoid the need for alignment of the mirrors which are optically contacted to the ends of the tube.

The external surface 22 of the glass tube 17 on the side facing the diffraction grating 16 is profiled to form a cylindrical lens focusing the radiation in one plane. The opposite external face 23 of the glass tube 17 is machined flat and polished. A silver or dielectric coating of high reflectivity at the wavelength of the pump radiation (532 nm) is applied to the surface 23 reflecting the partially focused pump radiation into the dye solution contained within the 3 mm bore of glass tube 17. The curvature of the front surface and the diameter of the tube are selected to reduce the beam diameter to ~2 mm at the centre of the tube. This arrangement allows a more uniform absorption of the pump radiation within the dye solution, leading to a better output beam quality and increased conversion efficiency. The dye concentration is adjusted to allow maximum absorption of the pump laser radiation by the dye solution while ensuring maximum uniformity of absorption within the dye tube cross-section. This concentration varies according to the dye selected. The appropriate concentration is first estimated using the absorption cross-section for the dye of interest at the pump wavelength, and is further optimised experimentally.

Following the excitation of the dye solution contained within the glass tube 17, secondary laser action occurs within the optical resonator formed by the two mirrors 21 sealing the ends of the tube. The high reflectivity mirror is chosen to have maximum possible reflectivity at the emission wavelength of the dye. The reflectivity of the partially reflecting mirror (output coupler) is chosen to maximise the energy extracted from the device. This reflectivity will be in the range 4% to 90% depending on the dye selected.

Due to the triplet state excitation and the long lifetime of this excited state (~1 s) it is essential continuously or repeatedly to replace the dye contained in the lasing region. The flow rate within the dye tube 17 is adjusted to allow at least one complete volume change within the 3 mm bore between each laser pulse. Addition of additives such as COT which quench the excited triplet state more rapidly can improve the performance of the device particularly when the device is operated at higher repetition rates.

Due to the photodegradability of the dyes, the dye solution contained within the device needs to be replaced after a given number of pulses. This varies depending on the pump pulse energy and the dye used in the device. The dye reservoir is easily interchangeable to permit quick change of the dye solution.

The beam produced by the device is focused by a lens 24 to produce the required energy density at a given distance from the end of the device. Easily interchangeable lenses would allow the spot size and the energy density to be varied over a very wide range.

The above side-pumping arrangement shows minimum sensitivity to the alignment of the pump beam and the articulated arm system, minimising power fluctuations due to slight misalignment in the articulated arm.

Figure 4:
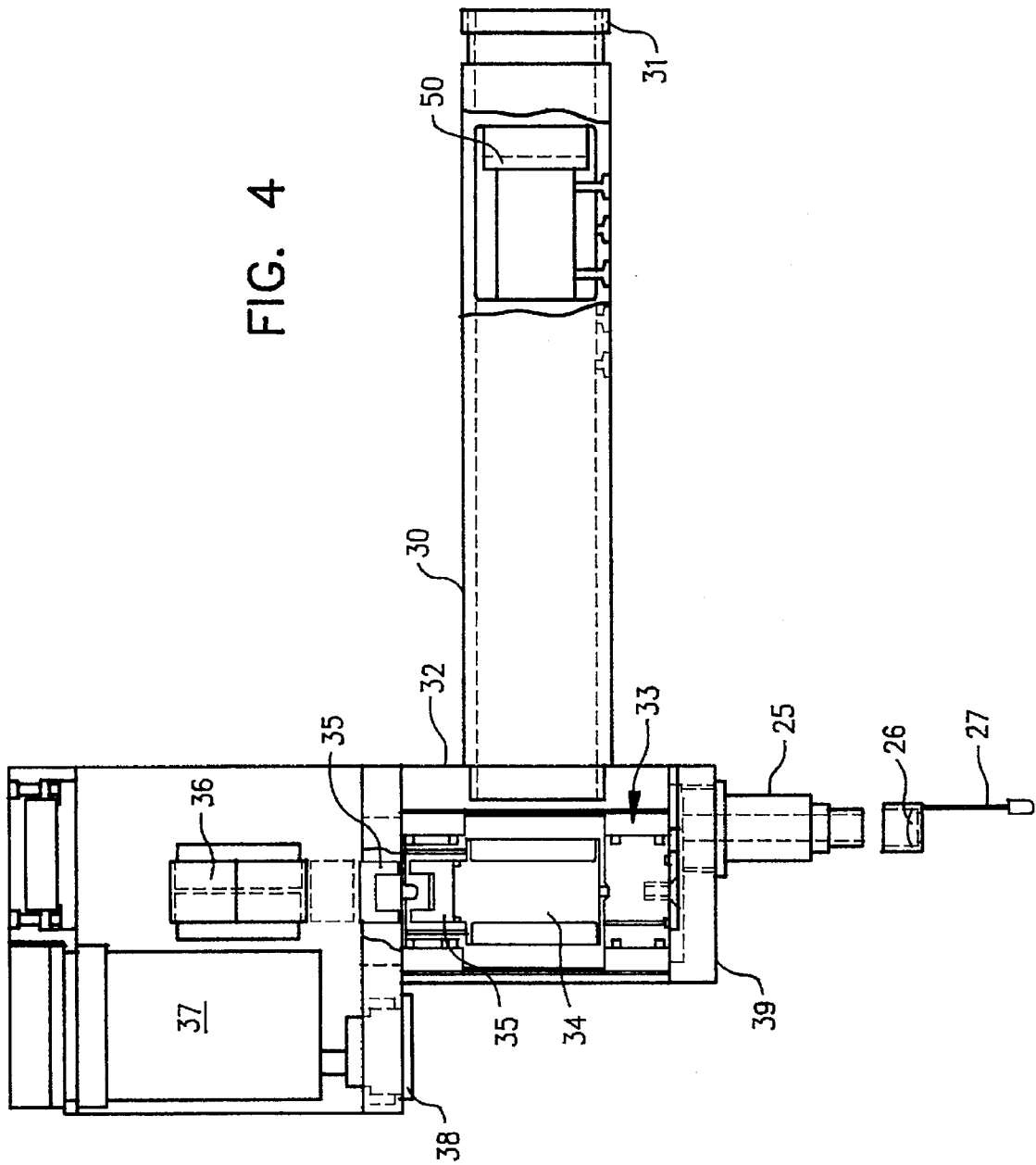
FIG. 4 is a part-sectional view of a third embodiment of the invention.

Referring now to FIG. 4 in a modified device, a modular housing 30 is adapted to be connected at 31 to an articulated arm system, itself connected to the pump laser. The housing 30 is connected to a further housing 32 which contains a dye cell generally indicated at 33, and has further attached an output housing 25 containing a lens 26 with a distal-end spacer 27 to ensure accurate placement of the device on the site to be treated. The dye cell 33 contains a spinning mechanism in the form of a rotary stirrer 34 which is driven in rotation about an axis normal to that of housing 30 and to the direction of the input light beam, by means of a non-contact magnetic drive coupling 35 rotated by an electric motor 36. A battery holder 37 and switch 38 for operation of the motor 36 are also enclosed within housing 32.

A mirror 40 is disposed at the rear end of housing 32 to enable laser action to take place within the dye cell 33.

Figure 5:
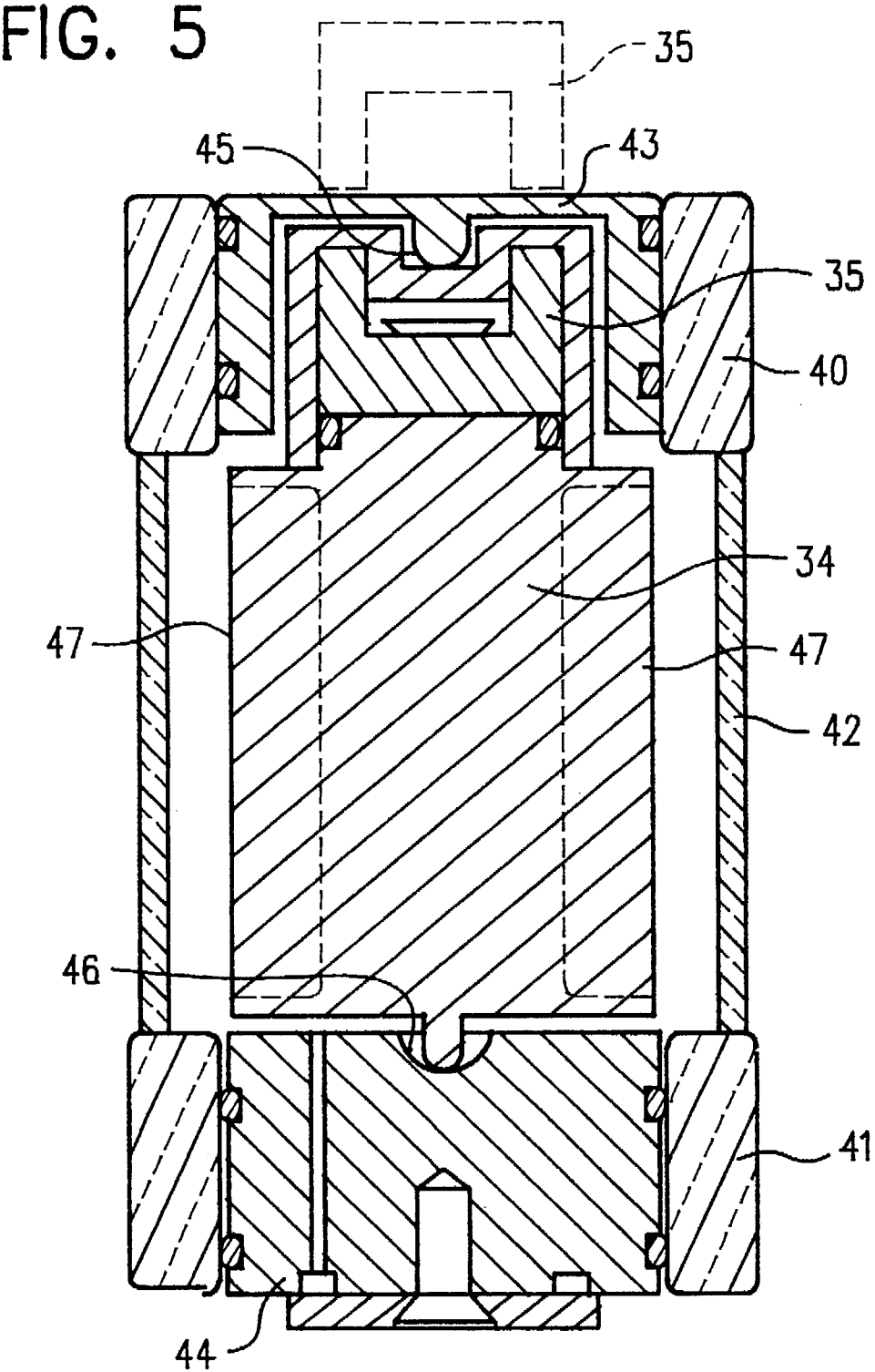
FIG. 5 is an enlarged cross-sectional view of a part of the embodiment illustrated in FIG. 4.

The enlarged drawing of FIG. 5 illustrates the details of the dye cell 33 which is removable from housing 32 by first removing an end cap 39 thereon. The dye cell has a transparent body comprising opposed annular parts 40 and 41 of quartz glass, each having an axial length in the region of 15 mm spaced apart by a distance of some 32 mm by means of a length of quartz tube 42 having a precision bore polished to remove any scratches and having an outer diameter of 34 mm and an inner diameter of 31 mm.

The ends of the body are closed by sealed plugs 43 and 44 having inwardly directed concave and convex bearing surfaces 45 and 46 respectively. Supported between these bearing surfaces is the rotary stirrer 34 in the form of a paddle having radial blades 47. Supported on its bearings the stirrer is free to rotate about the major axis of the cell in order to maintain continuous circulation of a dye solution contained within the cell.

Figure 3:
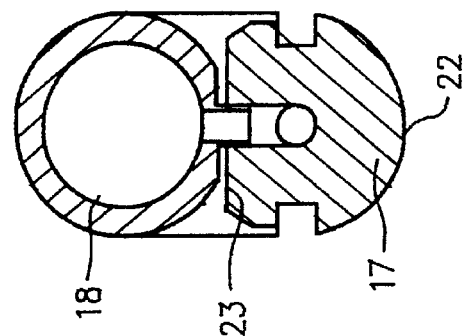
FIG. 3 is an enlarged cross-sectional view of a part of the embodiment illustrated in FIG. 2.

As in the embodiments of FIGS. 1 to 3, laser action at a predetermined wavelength takes place within the device as a result of no beam from the pump laser being transmitted via the articulated arm system into the housing 30 through a lens system 50 disposed therein, and passing through the wall 42 of the cell 33 to excite the dye solution within the latter such that lased light at the preselected frequency is transmitted from the device by the output lens 35.

In operation, the motor 36 is driven at a speed in the region of 2500 rpm. A gearbox (not shown) is used to reduce the motor speed by a ratio of 15:1, and to increase the torque. This gear ratio reduces the speed of the rotary stirrer 34 to approximately 3 revolutions per second which is considered to produce sufficient flow of the dye solution close to the cell wall to replace the dye volume in the pumped region between each laser pulse at a repetition rate of up to 10 Hz.

A variety of dyes may be used to produce a range of wavelengths. These include rhodamines, sulforhodamines, coumarins and others. Various solvents including water, methanol, ethanol and ethylene glycol may be included. Factors affecting the choice of solvent include solubility of the particular dye selected, dye lifetime requirements, efficiency requirements and dye viscosity requirements.

As an example, a solution of 0.25 grams of sulforhodamine 640 in one liter of methanol has been found to be the optimum solution for producing laser pulses at 650 nm with maximum efficiency and good beam quality.

The cell 33 which provides transverse flow i.e. the dye solution flows in a direction perpendicular to the lasing direction, allows more efficient and simpler replacement of the pumped dye volume between laser pulses. The system also has the advantage of being simple in construction, and the magnetic coupling of the motor to the cell allow simple and rapid exchange of dye cells for replacement and for wavelength selection.

The construction of the cell 33 is such that the dye solution comes into contact only with glass surfaces (items 40, 41 and 42) and with surfaces of PTFE adopted for the remaining interior construction of the cell. This ensures minimal contamination of the dye solution thus, in turn, improving its lifetime.

What is claimed is:

1. A device for producing laser light of a selectable wavelength comprising a primary laser; a multi-directional delivery system, the delivery system including a linear articulated arm; and a conversion device, the conversion device comprising a secondary laser having a lasing medium incorporating a fluid, and a circulation device further including spinning means disposed within the fluid for fluid circulation, the circulation device having a motor magnetically coupled to the spinning means for powering the spinning means, wherein a beam of primary laser light emitted from the primary laser is transmitted through the articulated arm and received by the conversion device, which emits a secondary laser beam of a different wavelength.

2. A device according to claim 1 wherein said fluid is a dye solution.

3. A device according to claim 2 wherein said dye solution is adapted to generate secondary laser radiation having a wavelength in the range 550 nm to 750 nm.

4. A device according to claim 2 wherein said dye solution is contained within a transparent tube.

5. A device according to claim 4 wherein said tube has end faces having reflective surfaces so as to form an optical resonator within the tube.

6. A device according to claim 4 further comprising a reservoir for containing said dye solution, wherein the circulation device circulates the dye solution from said reservoir in a flow through said tube.

7. A device according to claim 6 wherein said spinning means comprises an impeller disposed within said reservoir.

8. A device according to claim 6, wherein said primary laser is pulsed so as to cause the device to generate secondary laser light in pulses, the solution being circulated from the reservoir with circulation means adopted to produce a flow rate to allow at least one complete volume change within the tube between each secondary laser pulse.

9. A device according to claim 2 further comprising a diffraction grating disposed so as to direct a beam from the primary laser towards the tube so that said beam excites dye contained therein.

10. A device according to claim 9 wherein said tube has a first side facing said diffraction grating, said side being profiled to form a cylindrical lens to focus said beam in one plane.

11. A device according to claim 10 wherein said tube has a second side opposite said first side, said second side having a flat external surface which is polished and has a dielectric coating of high reflectivity at the wavelength of said beam.

12. A device according to claim 2, including a body removably attachable to the multi-directional delivery system and containing a removable, sealed, dye cell containing an organic dye solution, the the spinning means being disposed in the dye cell as a rotary stirrer which, in operation may be rotated continuously to circulate the dye solution within the dye cell.

13. A device according to claim 12, in which the stirrer is rotated by a non-contact magnetic drive coupling in turn rotated by an electric motor contained within the body.

14. A device according to claim 12, wherein the dye cell has a transparent body for transmission of the collimated beam from the primary laser.

15. A device according to claim 12, wherein the rotary stirrer is rotated at or in the region of three revolutions per second producing sufficient flow of the dye solution close to the cell wall to replace the dye volume in the pumped region between each secondary laser pulse at a repetition rate of up to 10 Hz.

16. A device according to claim 12, wherein the organic dye solution is comprised of 0.25 gm of Sulforhodamine 640 dissolved in one liter of methanol, producing laser pulses at 650 nm.

17. A device according to claim 12, wherein the several internal surfaces of the dye cell are quartz glass and PTFE respectively thus to ensure minimal contamination and thus maximum lifetime of the dye solution.

18. A device according to claim 7 in which said tube and said reservoir are contained within a cartridge which is removable from the device without removing the motor from the device.

19. A device according to claim 1, wherein the primary laser is a Q-switched, frequency doubled, Nd:YAG laser.

20. A device according to claim 1 wherein the secondary laser beam is focussed by a lens to provide a predetermined beam diameter on a surface at a given distance from the device.

21. A device according to claim 1 wherein a lens system transmitting the collimated beam of given wavelength to the conversion means consists of a 200 mm focal length spherical lens and a 50 mm focal length cylindrical lens each coated for anti-reflection to ensure minimal loss.

22. A device for producing laser light of a selectable wavelength, comprising a primary laser; a multi-directional delivery system in the form of a linear articulated arm having a distal end; and a modular conversion device removably attachable to the distal end of the linear articulated arm; the conversion device including a secondary laser having a solid or fluid lasing medium, wherein when the conversion device is attached to the distal end of the articulated arm of the primary laser, a beam of primary laser light emitted from the primary laser is received by the conversion device, causing the secondary laser to emit a secondary beam of laser light having a wavelength different than the wavelength of the primary laser light, the device thereby being operable for producing laser light of at least two different wavelengths by removably attaching and detaching the conversion device to the distal end of the linear articulated arm.

23. A device according to claim 22, wherein the lasing medium is a non-linear optical crystal.

24. A device according to claim 23, wherein the lasing medium is a titanium doped sapphire crystal.

25. A device according to claim 23, wherein the crystal is positioned to have opposed end faces which are perpendicular to the axis of the device, the proximal end face of the crystal having a dielectric coating of low reflectivity at 532 nm and maximum reflectivity at 790 nm, and the distal end of the crystal having a dielectric coating of partial reflectivity at 790 nm, such that the crystal end faces form an optical resonator creating secondary laser action in the optically excited crystal material.

26. A device according to claim 25, wherein high damage threshold coatings are provided to avoid optical damage from the primary laser radiation on the proximal end face of the crystal, and from the secondary laser radiation on the distal end face thereof.

27. A device according to claim 23, wherein the crystal length is in the range 5 mm to 50 mm and the dopant concentration is in the range 0.05% to 0.25%.

28. A device according to claim 23, wherein the primary laser includes a quarter wave plate to convert the linear polarisation of the primary laser into circular polarisation before entering the delivery system.

* * * * *